United States Patent [19]

Fullen et al.

[11] Patent Number: 5,323,650
[45] Date of Patent: Jun. 28, 1994

[54] SYSTEM FOR CONTINUOUSLY MEASURING FORCES APPLIED TO THE FOOT

[75] Inventors: George Fullen, Littleton, Colo.; Jeryl G. Fullen, Newton, Kans.

[73] Assignee: Fullen Systems, Inc., Littleton, Colo.

[21] Appl. No.: 4,732

[22] Filed: Jan. 14, 1993

[51] Int. Cl.$^5$ ............................................. A61B 5/103
[52] U.S. Cl. ................................... 73/172; 73/865.07; 128/779
[58] Field of Search .......................... 73/172, 865.07; 338/114; 128/779

[56] References Cited

U.S. PATENT DOCUMENTS

| | | |
|---|---|---|
| 3,791,375 | 2/1974 | Pfeiffer . |
| 3,974,491 | 8/1976 | Sipe . |
| 4,734,034 | 3/1988 | Maness et al. . |
| 4,745,930 | 5/1988 | Confer ................................ 128/779 |
| 4,813,436 | 3/1989 | Au . |
| 4,856,993 | 8/1989 | Maness et al. . |
| 4,862,743 | 9/1989 | Seitz ........................... 73/862.04 X |
| 5,033,291 | 7/1991 | Podoloff et al. . |
| 5,079,949 | 1/1992 | Tamori ................................ 73/172 |

FOREIGN PATENT DOCUMENTS

| | | |
|---|---|---|
| 2656864 | 5/1978 | Fed. Rep. of Germany . |
| 3631923 | 3/1988 | Fed. Rep. of Germany . |

OTHER PUBLICATIONS

"Leg Load Warning System for the Orthopedically Handicapped," Medical and Biological Engineering (May, 1974) by Donald Endicott et al.

S. Miyazaki and H. Iwakura, "Foot-Force Measuring Device for Clinical Assessment of Pathological Gait," Medical and Biological Engineering and Computing (Jul., 1978).

G. A. Spolek and F. G. Lippert, "An Instrumented Shoe—A Portable Force Measuring Device," J. Biomechanics (Great Britain, Jun., 1976).

John A. Purbrick, "A Force Transducer Employing Conductive Silicon Rubber," First Robot Vision and Sensors Conferences, Stratford-on-Avon, England (Apr., 1981).

*Primary Examiner*—Daniel M. Yasich
*Attorney, Agent, or Firm*—Sheridan Ross & McIntosh

[57] ABSTRACT

A self-contained system for measuring forces applied to the foot of a user includes a force sensor array positioned within the user's shoe between the foot and the inner sole of the shoe, the force sensor array including a multiplicity of individual force sensors arranged in a pattern that covers the entire area of contact between the sole of the user's foot and the inner sole of the shoe, an electronic circuit module removably attached to the side of the shoe, and a flat interconnecting cable for electrically coupling the force sensor array to the electronic circuit module. The electronic circuit module includes a central processing unit, read-only memory, random access memory, and scanning circuitry for electronically continuously scanning the force sensor array to obtain information indicative of an instantaneous force sensed by each one of the multiplicity of individual force sensors of the force sensor array, for processing that information to obtain force data, and for storing the force data in the random access memory. An annunciator audibly signals the user when a force on the foot greater than a predetermined threshold force is sensed.

8 Claims, 9 Drawing Sheets

SYSTEM FOR CONTINUOUSLY MEASURING FORCES APPLIED TO THE FOOT

BACKGROUND AND SUMMARY OF THE INVENTION

This invention relates generally to foot pressure sensors and more particularly to a system that may be employed by orthopedic surgeons, their patients, physical therapists, athletes, coaches, trainers, and others to measure forces applied to the foot.

Controlling the weight placed on an affected leg while moving about can prevent injury and speed recovery of patients recovering from certain trauma or orthopedic procedures. A person is able to perceive a changing relative weight on a foot, but cannot reliably sense how much constant weight is actually being loaded. That is, an individual's own senses cannot reliably detect how much actual constant weight he or she is placing on a foot. This essential weight information must therefore be provided by some type of external or artificial device.

Forces applied to the foot are not always evenly distributed over the entire surface or sole of the foot. They are usually, but not always, concentrated at the heel or ball of the foot, and they are also usually not applied to these two areas at the same time. A typical walking or running foot strike first loads the heel and then the ball of the foot. In other situations, such as when performing an athletic maneuver, the weight placed on the foot will shift in different patterns. The specific location on the sole of the foot where forces are present, the times at which those forces occur, and the magnitude of those forces are of interest in a number of situations.

Many devices have been designed to measure forces applied to the foot. These include devices for measuring applied forces that are coincident with the position of the leg and body during walking or running, for measuring peak pressure to alert sensory impaired individuals such as diabetics, for measuring the total force applied to the foot, and for measuring forces applied to certain areas of the foot for various purposes.

Such prior art foot force measurement devices are typically heavy and cumbersome and, thus, act to restrict the wearer's movements. Devices which employ an electronic package strapped to the wearer's leg above the ankle and electrically connected to a foot sensor require extra effort when attaching or removing the device. Although this extra effort may seem insignificant, it is nevertheless an inconvenience that may prompt wearer's of such devices to neglect their use. Further, these bulky prior art devices chafe the wearer's skin, are prone to snagging, and are subject to failure resulting from stress on the electrical cable that connects the electronic package to the foot sensor. Other prior art devices employ a stationary foot sensor pad and are therefore only suited for use in a laboratory.

All of the known foot force measurement devices function to convert mechanical force into a suitable signal medium, usually electrical signals. Consequently, the prior art can be conveniently categorized according to the type of sensor used to convert changes in mechanical force to changes in electrical signals. Accordingly, these types of prior art sensors include pneumatic or hydraulic fluid activated switches, strain gauge sensors that respond to mechanical deformation, single direct electronic force sensors, multiple direct electronic force sensors with random spacing, and multiple direct electronic force sensors with regular spacing.

Pneumatic and hydraulic sensors are prone to produce inaccurate readings because changes in internal pressure are not necessarily proportional to changes in force. An accurate hydraulic sensor can be constructed if the fluid is displaced from a containing structure which itself, not the fluid, supports the applied forces, and the force required to activate a switch or sensor is very small compared to the force being measured. Exemplary of such prior art sensors are those taught in German patent 3631-923-A to Ernst and in U.S. Pat. No. 3,974,491 to Sipe. Another way to construct an accurate fluid sensor is to use rigid plates which limit the applied force to a constant area of fluid contact, as taught in U.S. Pat. No. 3,791,375 to Pfeiffer. In such sensors, the fluid pressure is proportional to the applied force. However, these sensors are disadvantageous due their bulkiness and weight.

The sensors which measure mechanical deformation of structural elements supporting the wearer's foot by use of electrical wire or ribbon type strain gauges accurately measure weight, but they are also disadvantageous because of their bulk and weight. Exemplary of these prior art sensors are those taught by Donald Endicott et al., "Leg Load Warning System for the Orthopedically Handicapped," Medical and Biological Engineering (May, 1974) S. Miyazaki and H. Iwakura, "Foot-Force Measuring Device for Clinical Assessment of Pathological Gait," Medical and Biological Engineering and Computing (July, 1978), and G. A. Spolek and F. G. Lippert, "An Instrumented Shoe-A Portable Force Measuring Device," J. Biomechanics (Great Britain, June, 1976).

All of the below-mentioned direct electronic force sensor devices are essentially identical to a type of microphone used in telephones. In this prior art device, the acoustic force compresses a partially conductive material (carbon granules) and therelay reduces its electrical resistance. A force sensor based on this concept can be constructed by forming thin electrodes on two plastic films and then covering the electrodes with a thin layer of suitable partially conductive material. When the two coated films are positioned sot that the two layers of partially conductive material are in contact, the electrical resistance through the sensor from electrode to electrode varies inversely with a compressing force on the sensor. This is because as the coating is pressed with greater force, the electrical current path becomes broader due to increased area of contact. This effect occurs with any conductive material, but materials useful as active elements in practical force sensors must have a relatively high electrical resistance. Such thin film electronic force sensors have the advantages of simplicity, compactness, and light weight.

Single direct electronic force sensors, such as that taught in German patent 2656-864, cannot be corrected for variations in response from one part of the sensor to another. They cannot separately measure forces on different parts of the foot. It is also possible that simple bending of this type of sensor will produce a signal inappropriately indicating an applied force.

The multiple direct electronic force sensor system taught in U.S. Pat. No. 4,813,436 to Au measures forces only where the individual sensors are attached to the foot. If the measurements are used to compute total force applied to the foot and are variously spaced, the contributory area of each sensor must be used in the necessary computation of the total force applied. This prior art system is disadvantageous in that the relative position of each sensor must be separately determined for each person on which the sensor is used.

This problem is solved by the multiple direct electronic force sensors taught in U.S. Pat. Nos. 4,734,034 and 4,856,993 to Maness et al. and U.S. Pat. No. 5,033,291 to Podoloff et al. in which the sensors are regularly spaced. Since the relative position of each sensor is fixed, a mathematical description of the location of each sensor can easily be made part of a permanent computer database. These sensor arrays are very thin and very light weight, but they cannot conform to a compound curved surface without wrinkling. Such wrinkled or folded thin film sensor arrays will produce erroneous results. For example, if the sensor array is folded so that two separate sensors are positioned one above the other, they both measure the same force. This is an obvious error. A folded sensor array may produce an electrical signal from the folding alone, another obvious error. Folding or wrinkling also subjects the sensor array to severe fatigue, stress, which can lead to early and sudden failure.

A practical sensor array preferably includes several hundred individual force sensors. The problem of electrically connecting this number of individual sensors to data acquisition circuitry is a significant one. A simple connection scheme would require as many electrical connections to the circuitry as sensors, plus one common connection. However, the circuitry described by John A. Purbrick, "A Force Transducer Employing Conductive Silicon Rubber," First Robot Vision and Sensors Conferences, Statford-on-Avon, England (April, 1981), makes a more efficient connection method possible. This prior art circuit can measure current through individual force sensors in a two-vector array of rows and columns with a top electrode of all sensors in each column commonly connected and a bottom electrode of all the sensors in each row likewise commonly connected. If such an array has equal numbers of columns and rows, the number of connections to circuitry is reduced to twice the square root of the number of sensors. The Purbrick method is not as efficient when employing other ratios of columns to rows of sensors, but it nevertheless represents the most efficient method known for interconnecting the sensor array of the present invention. A similar method is taught by W. D. Hillis, "Active Touch Sensing," Artificial Intelligence Laboratory Memo 629, M.I.T. (April, 1981).

It is therefore a principal object of the present invention to provide a self-contained force measurement system for continuously sampling the magnitude and distribution of forces that are present on the bottom of one or both feet of the user when engaged in various activities.

It is a further object of the present invention to provide such a force measurement system that does not unduly impede walking, running or other ordinary movements of the user.

It is a further object of the present invention to provide such a force measurement system that is self-contained for use away from a laboratory or clinic and that is capable of annunciating appropriate weight bearing conditions, of generating computer data for future reference and analysis, and of transmitting this computer data by wireless means to remotely located equipment.

These and other objects of the present invention provide a force measurement system useful to the medical patient, attendant physician, physical therapist, prosthetist, orthotist, podiatrist, athlete, sports trainer, coach or research professional interested in carefully studying or managing a wide range of problems of the human lower extremity.

DETAILED DESCRIPTION OF THE PREFERRED EMBODIMENT

Figure 1:
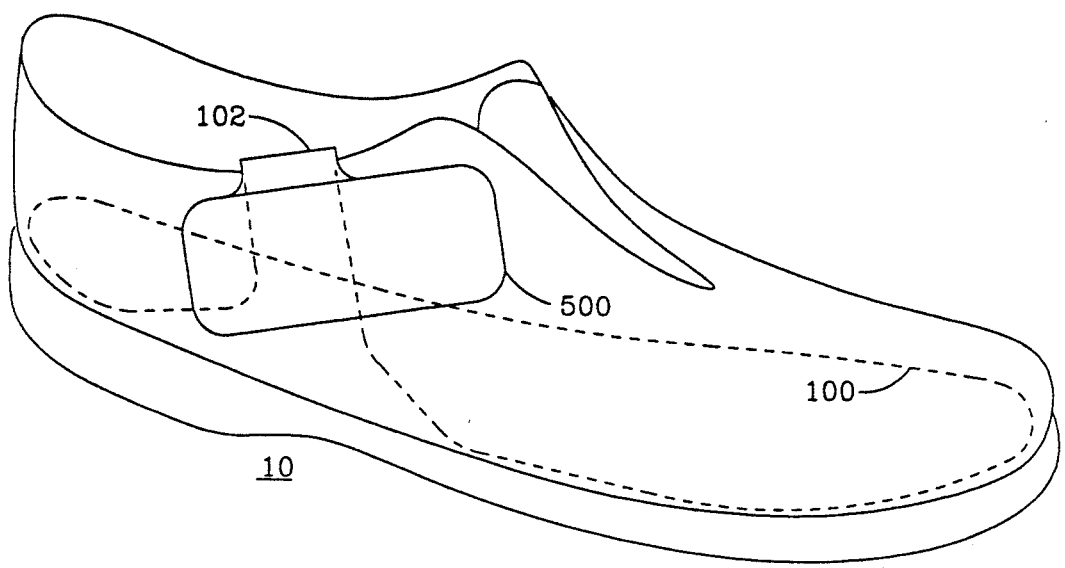
FIG. 1 is a pictorial diagram of a shoe fitted with a force sensor array and an interconnected electronic circuit module in accordance with the present invention.
Figure 2:
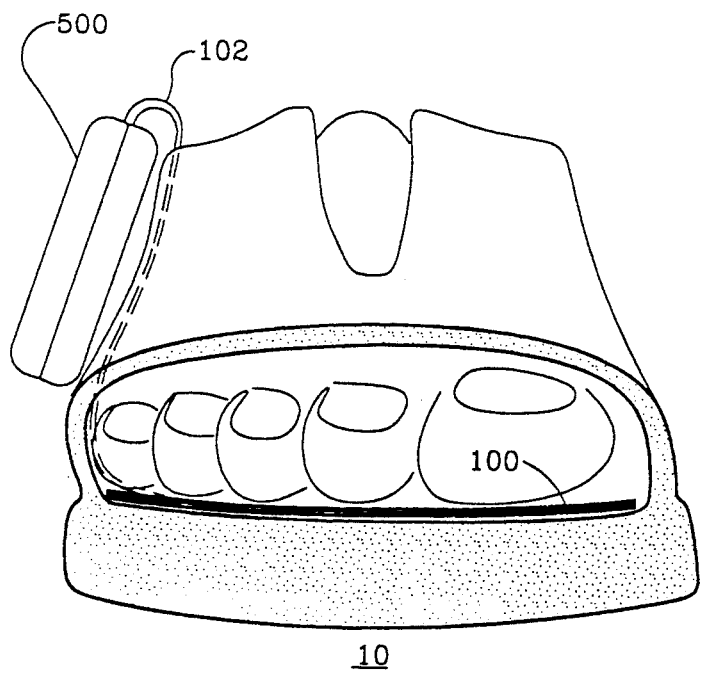
FIG. 2 is a partial sectional pictorial diagram of the shoe of FIG. 1 illustrating the position of the force sensor array within the shoe.

Referring now to FIGS. 1 and 2, there is shown a shoe 10 containing a force sensor array 100 and an electronic circuit module 500 connected thereto by means of a flat ribbon cable 102. Force sensor array 100 is arranged to cover the entire area of contact between the bottom of the wearer's foot and shoe 10. Electronic circuit module 500 is preferably clipped or otherwise attached to the side of shoe 10 that is opposite the other foot and slightly forward of the center thereof, where it is least likely to be damaged or to interfere with the normal physical activities of the wearer.

Figure 3:
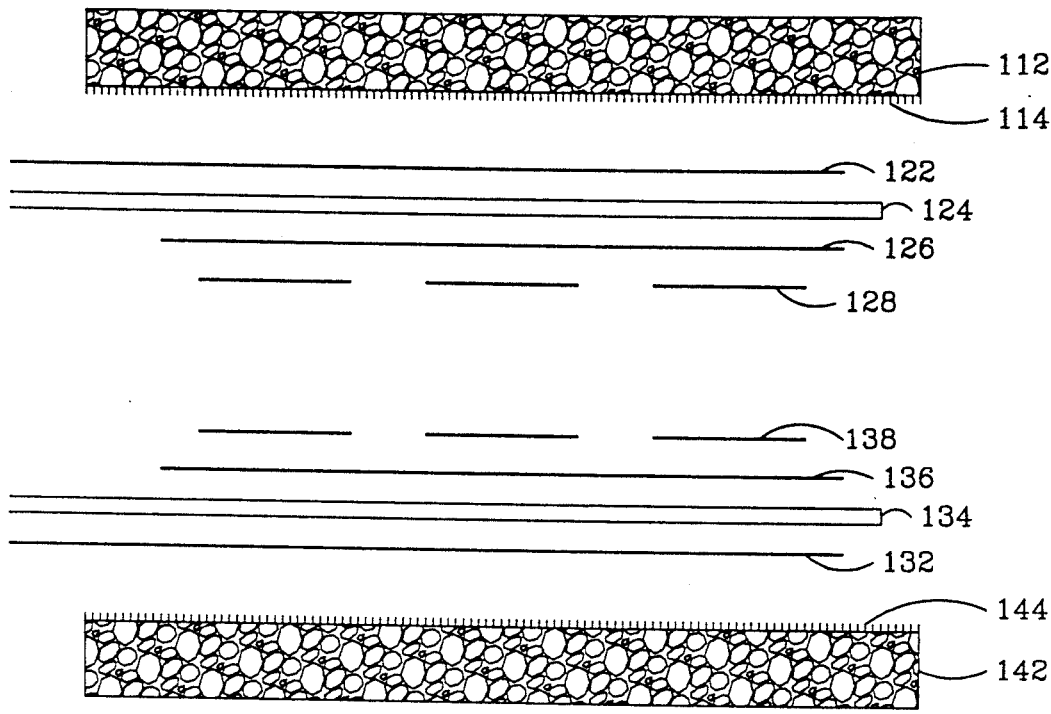
FIG. 3 is an exploded sectional diagram of the force sensor array employed within the shoe of FIGS. 1 and 2.

Referring now to FIG. 3, covering layers 112 and 142 are used to hold the remaining parts of the force sensor array 100 together and to isolate them from contamination. Covering layers 112 and 142 may comprise, for example, a 1/16-inch thick, adhesive coated, closed cell vinyl foam tape such as 3M Scotchfoam 4726. A conductive trace layer 122 comprises a multiplicity of conductive traces, each of which is electrically connected through a substrate 124 to each line of a multiplicity of lines of sensor electrodes that are formed by a conductive trace layer 126 and a like number of contact points that are also formed by conductive trace layer 126. Similarly, a conductive trace layer 132 comprises a multiplicity of conductive traces, each of which is electrically connected through a substrate 134 to each line of a multiplicity of lines of sensor electrodes formed by another conductive trace layer 136. Conductive trace layers 122, 126, 136, and 132 may comprise any suitable electrically conductive material capable of being printed or otherwise deposited on substrates 124, 134. Substrates 124, 134 are thin flexible dielectric films and may comprise, for example, Dupont Kapton polyimide film material. Other films may also be used. Pressure sensitive coating layers 128, 138 may comprise a commercially available partially conductive pressure sensitive coating, such as one of those designated as numbers 4407 and 4408 produced by Chomerics, Inc. of Woburn, Mass.

Figure 4:
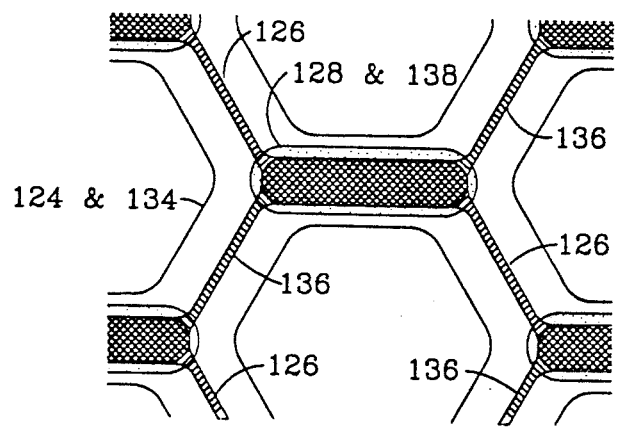
FIG. 4 is a detailed diagram of a portion of the force sensor array of FIG. 3 illustrating the planar arrangement of the conductive traces forming the top and bottom sensor electrodes and their relationship to pressure sensitive conductive coatings and removed areas of the substrates.

Referring now to FIG. 4, hexagonal areas of the substrates 124, 134 are removed to increase the elasticity of the assembled force sensor array 100, allow it to stretch, provide mechanical isolation for the individual sensors comprising force sensor array 100, and allow contact of the adhesive coatings 114, 144. Conductive trace layers 126, 136, which form individual force sensor electrodes, are prevented from directly contacting each other by the position and shape of pressure sensitive coatings 128, 138. The areas of the partially conductive pressure sensitive coatings 128, 138 are slightly larger than the sensor electrode areas, and the conductive traces connecting the individual force sensor electrodes not covered by the pressure sensitive coatings do not come into contact because their positions are not coincident. The film substrates 124, 134 between the hexagonal removed areas are only wide enough to accommodate the various conductive traces, electrodes, and sensor areas. Narrower bands of the film substrates 124, 134 between the individual force sensors of force sensor array 100 result in greater flexibility and elasticity and provide better mechanical isolation of the individual sensors.

Figure 5:
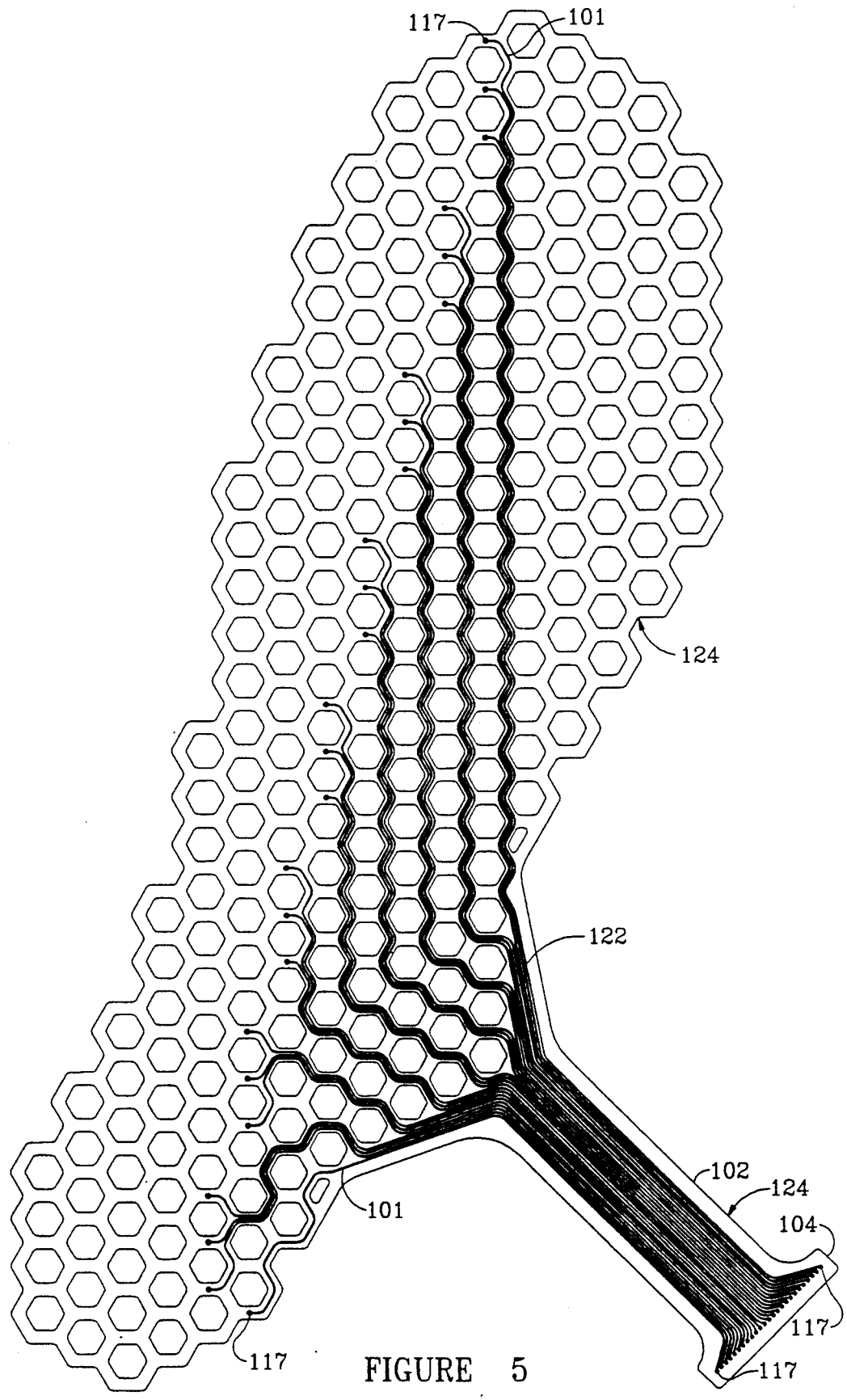
FIG. 5 is a detailed diagram illustrating conductive traces on a top surface of a top substrate of the force sensor array of FIG. 3.
Figure 6:
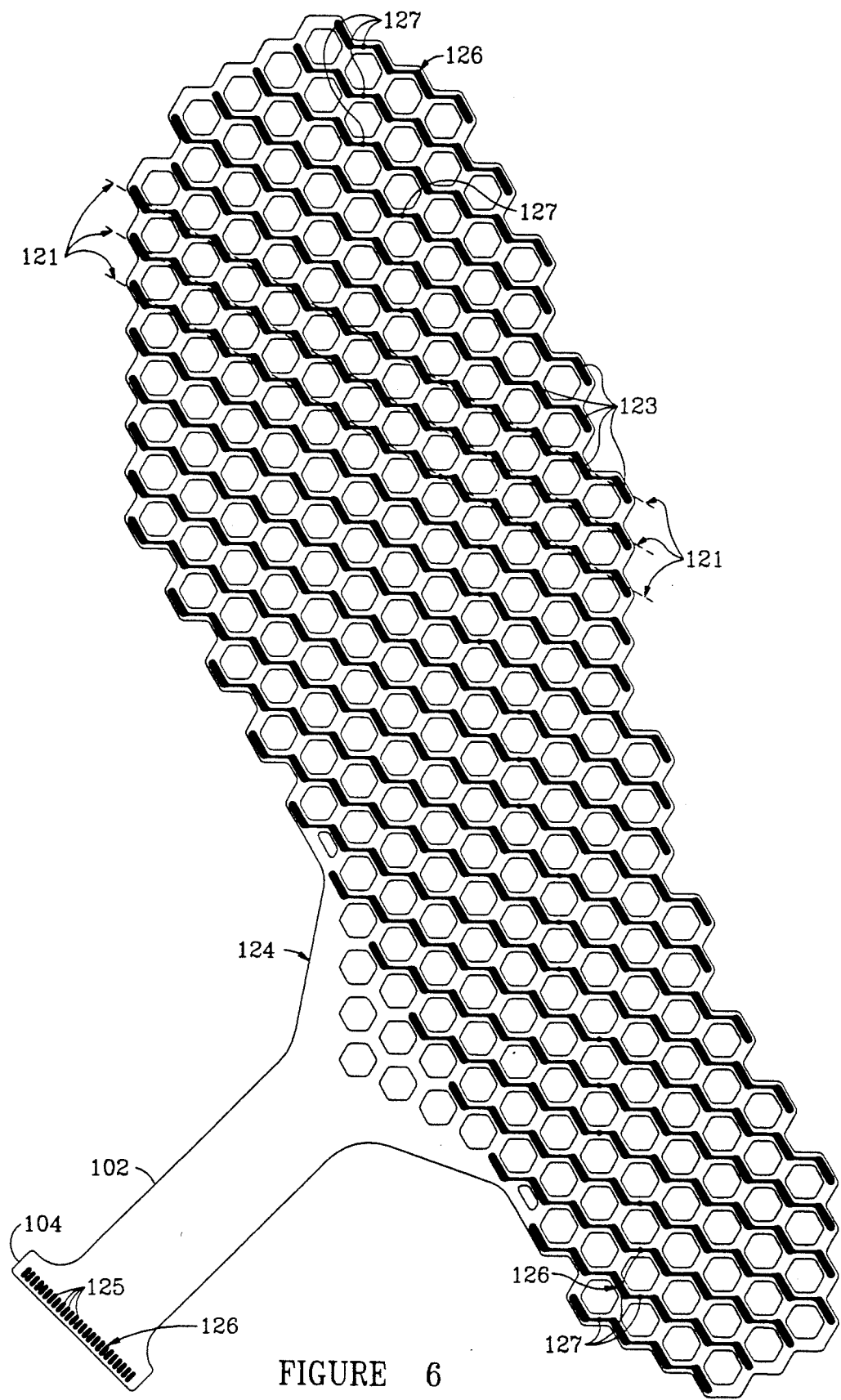
FIG. 6 is a detailed diagram illustrating conductive traces on a bottom surface of the top substrate of the force sensor array of FIG. 3.

Referring now to FIGS. 5 and 6, conductive trace layer 122 on the top surface of film substrate 102 connects each diagonal line 121 of individual force sensor electrodes 123 formed by conductive trace layer 126 to the electronic circuit module 500 of FIGS. 1 and 2. Electrical connections through the film substrate 124 to conductive trace layer 126 on the bottom surface of film substrate 102 are under enlarged areas 117 at both ends of each conductive trace 101 of conductive trace layer 122.

Referring now to FIG. 6 conductive trace layer 126 forms diagonal lines 121 of sensor electrodes 123 and contact area 125 for connection to the electronic circuit module 500. Electrical connections through the substrate 124 to conductive trace layer 122 on the top surface of film substrate 124 are under enlarged areas 127 between the force sensor electrodes 123 and also under the contact areas 125 in connector tab 104. Thus, all of the individual force sensor electrodes 123 in a diagonal line 121 are commonly connected through a single conductive trace 101 of conductive trace layer 122 to electronic circuit module 500.

Figure 7:
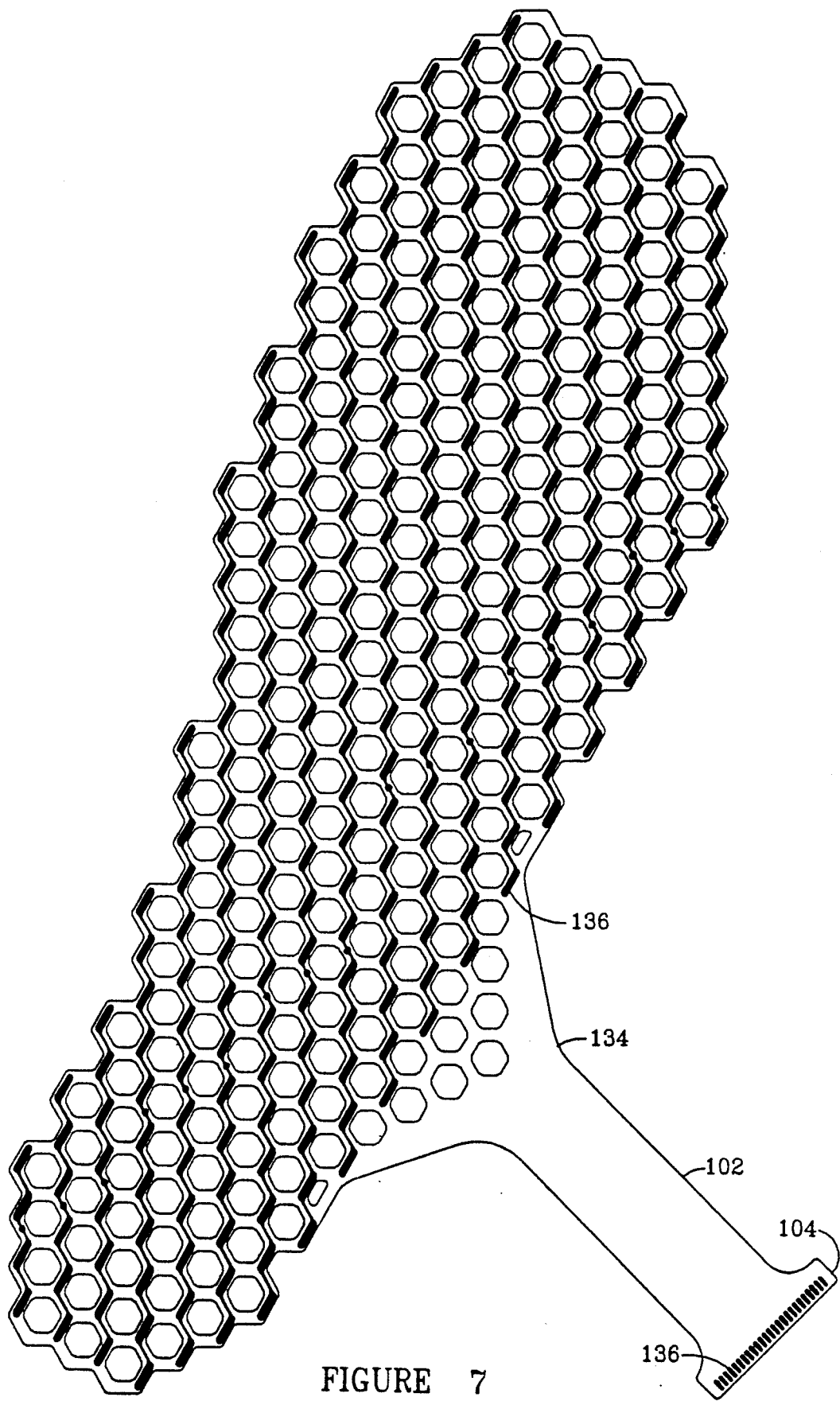
FIG. 7 is a detailed diagram illustrating conductive traces on a top surface of a bottom substrate of the force sensor array of FIG. 3.

Referring now to FIG. 7, conductive trace layer 136 forms lines of individual force sensor electrodes and contacts for connection to the electronic circuit module 500. Electrical connections through the substrate 134 to conductive layer 132 are under enlarged areas between the individual force sensor electrodes and also under the contact areas of conductive trace layer 136 in connector tab 104. Thus, all of the individual force sensor electrodes in a line are commonly connected through a single conductive trace of conductive trace layer 132 to electronic circuit module 500.

Figure 8:
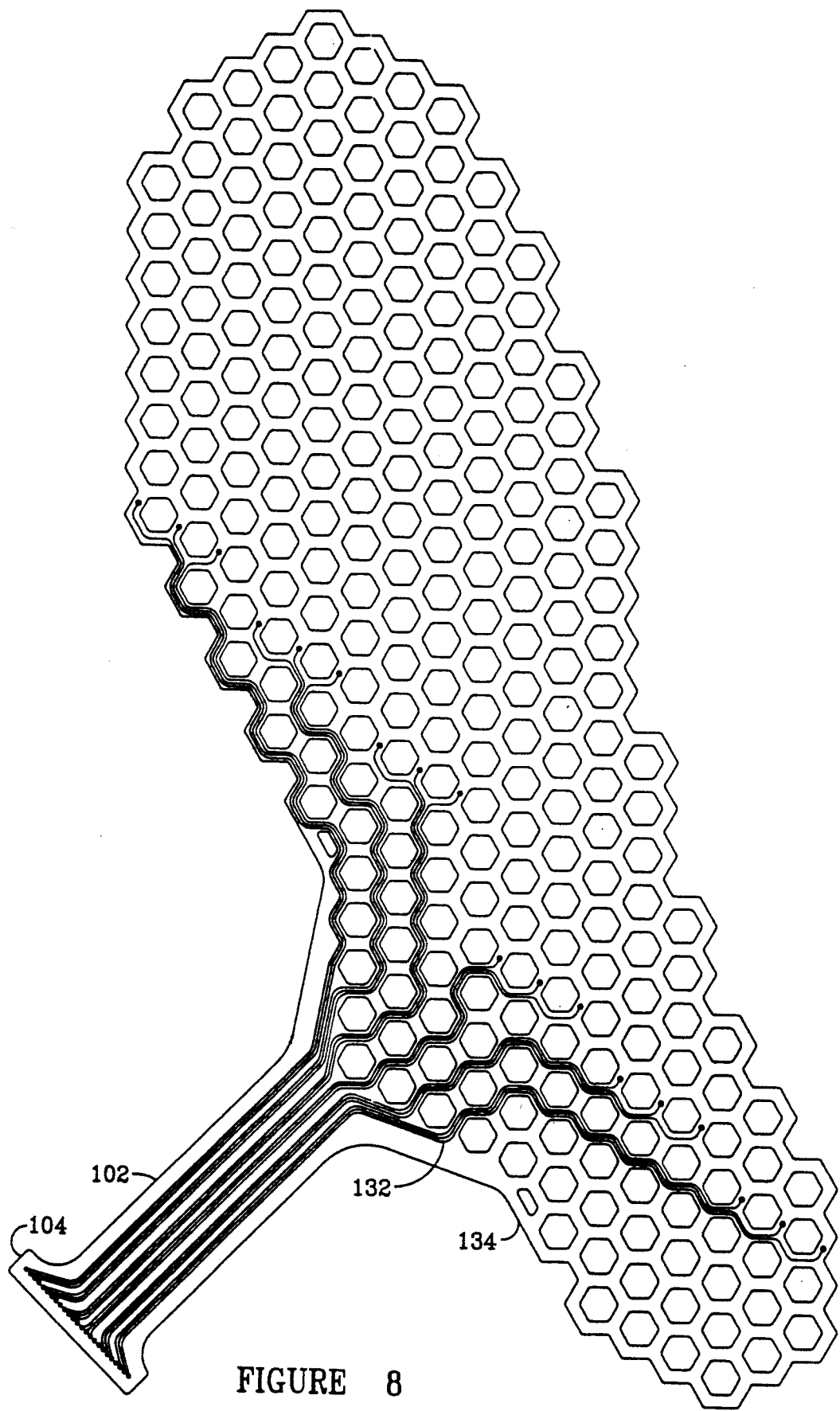
FIG. 8 is a detailed diagram illustrating conductive traces on a bottom surface of the bottom substrate of the force sensor array of FIG. 3.

Referring now to FIG. 8, conductive traces of conductive trace layer 132 connect each line of individual force sensor electrodes formed by conductive trace layer 136 to the electronic circuit module 500. Electrical connections through the substrate 134 to conductive trace layer 136 are under enlarged areas at both ends of each trace of layer 132.

Referring now generally to FIGS. 5-8, the layout of the force sensors 128, 138, lines of individual force sensor electrodes formed by conductive traces of conductive trace layers 126, 136, and conductive traces 122, 132 permit trimming the array to fit various shoe sizes. The diagonal arrangement of force sensors 128, 138 results in a smaller number of electrical leads in conductive trace layers 122, 132 than would be required if the sensors 128, 138 were perpendicularly arranged. This is because the ratio of the length to width of the human foot is about 3.5, and a similar ratio of rows to columns would result. In the diagonal sensor layout of the present invention, the ratio of rows to columns can be closer to unity. The honeycomb pattern of the substrates produces meandering, nonlinear courses for electrical conductive leads in conductive trace layers 122, 132. This prevents a stiff conductive material such as copper from excessively restricting the stretching of the force sensor array 100 along the general direction of the leads.

Figure 9:
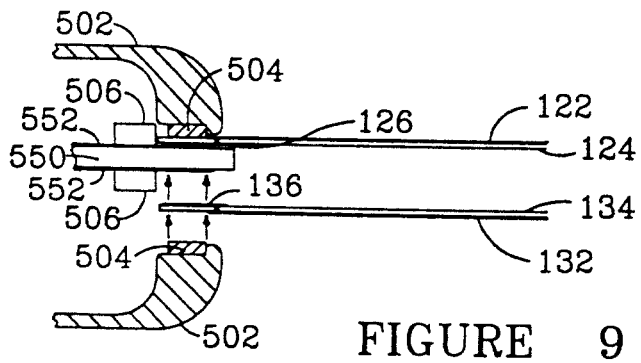
FIG. 9 is a sectional diagram illustrating the details of the interconnection between the force sensor array and electronic circuit module of FIGS. 1 and 2.
Figure 10:
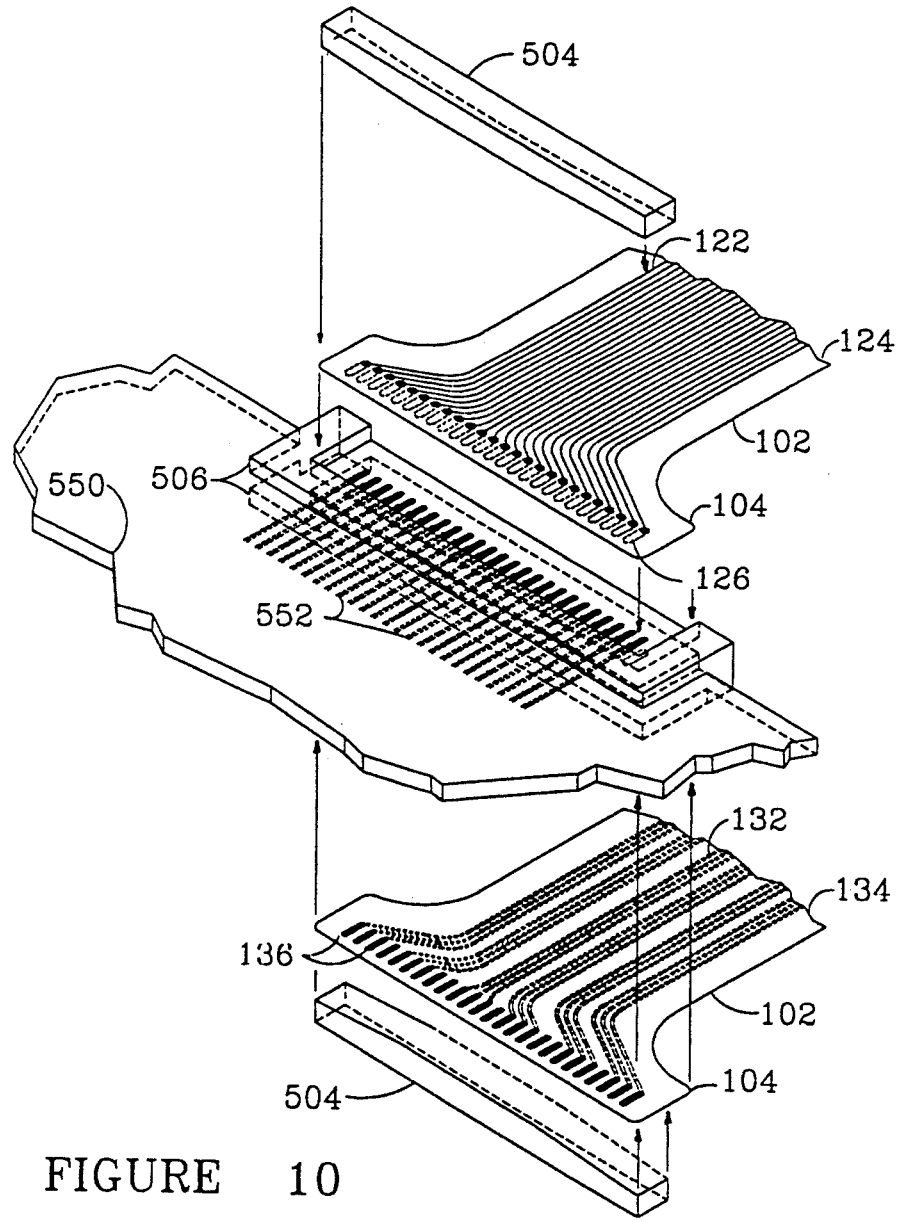
FIG. 10 is an exploded pictorial diagram of the interconnection of FIG. 9.

Referring now to FIGS. 9 and 10, a portion of a standard two-sided printed circuit board 550 extends to the exterior periphery of electronic circuit module 500, together with conductive leads 552 to form contacts arranged to coincide with contact areas of electrode lines formed by conductive trace layers 126, 136. The connector portion of force sensor array 100 and the printed circuit board 550 are clamped between facing halves 502 of electronic circuit module 500. Any conventional mechanical fastening device may be used to hold the facing halves 502 of electronic circuit module 500 together. Elastic material 504 evenly distributes the clamping force. A thickened center of elastic material 504 compensates for any bending that may take place in the two facing halves 502 of electronic circuit module 500. Guides 506 position the end portions of the force sensor array 100, while the two facing halves 502 of electronic circuit module 500 are tightened. The clearance between the connector parts 104 of substrates 124, 134 to guides 506 is small enough to assure alignment between each of the connector contact areas of electrode lines formed by conductive trace layers 126, 136 and contact areas 552. The conductive traces of conductive trace layers 122, 132 are as closely spaced as practical to make the cable 102 portion of substrates 124, 134 as narrow as possible. Curving the re-entrant edges of substrates 124, 134 reduces fatigue stress.

Figure 11:
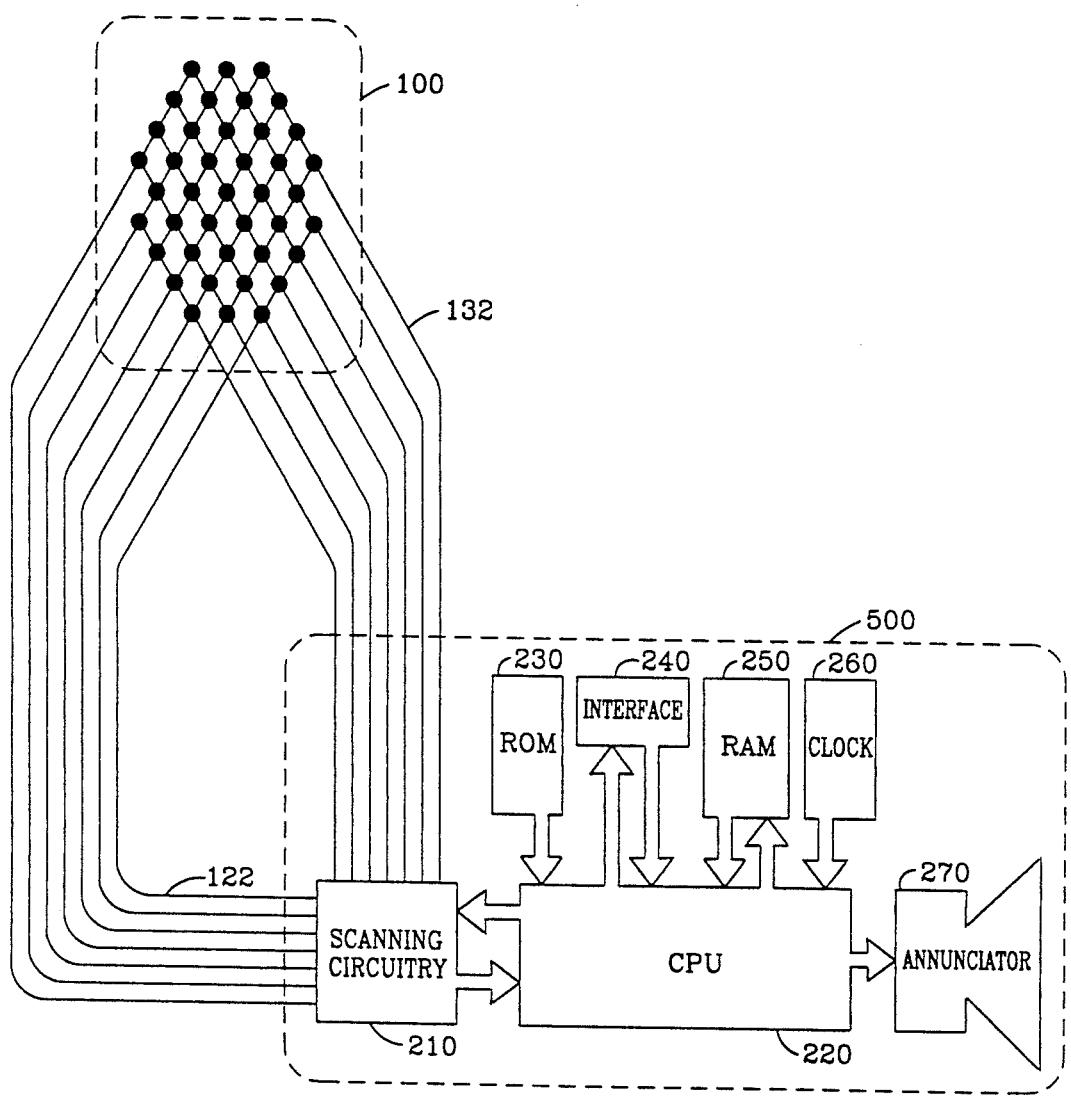
FIG. 11 is a block diagram of circuitry employed in the electronic circuit module of FIGS. 1 and 2.

Referring now to FIG. 11, force sensor array 100 is connected to electronic circuit module 500, which contains scanning circuitry 210 controlled by a central processing unit (CPU) 220. CPU 220 executes software routines stored in a read-only memory (ROM) 230 during system boot and thereafter executes software programs stored in a random access memory (RAM) 250. An interface 240 is used to up-load data stored in RAM 250 to an external personal computer (PC) and to download operational data and software programs from a PC to RAM 250. A time of day and calendar clock 260 provides time and date information to CPU 220. An annunciator 270 is controlled by CPU 220 for signalling the occurrence of measured forces exceeding preset thresholds, hardware fault conditions, and operator errors. Alternatively, annunciator 270 may be replaced by a wireless data transmitter to interface electronic circuit module 500 to external electronic equipment for the purpose of transferring data and other information between electronic circuit module 500 and the external electronic equipment.

Figure 12:
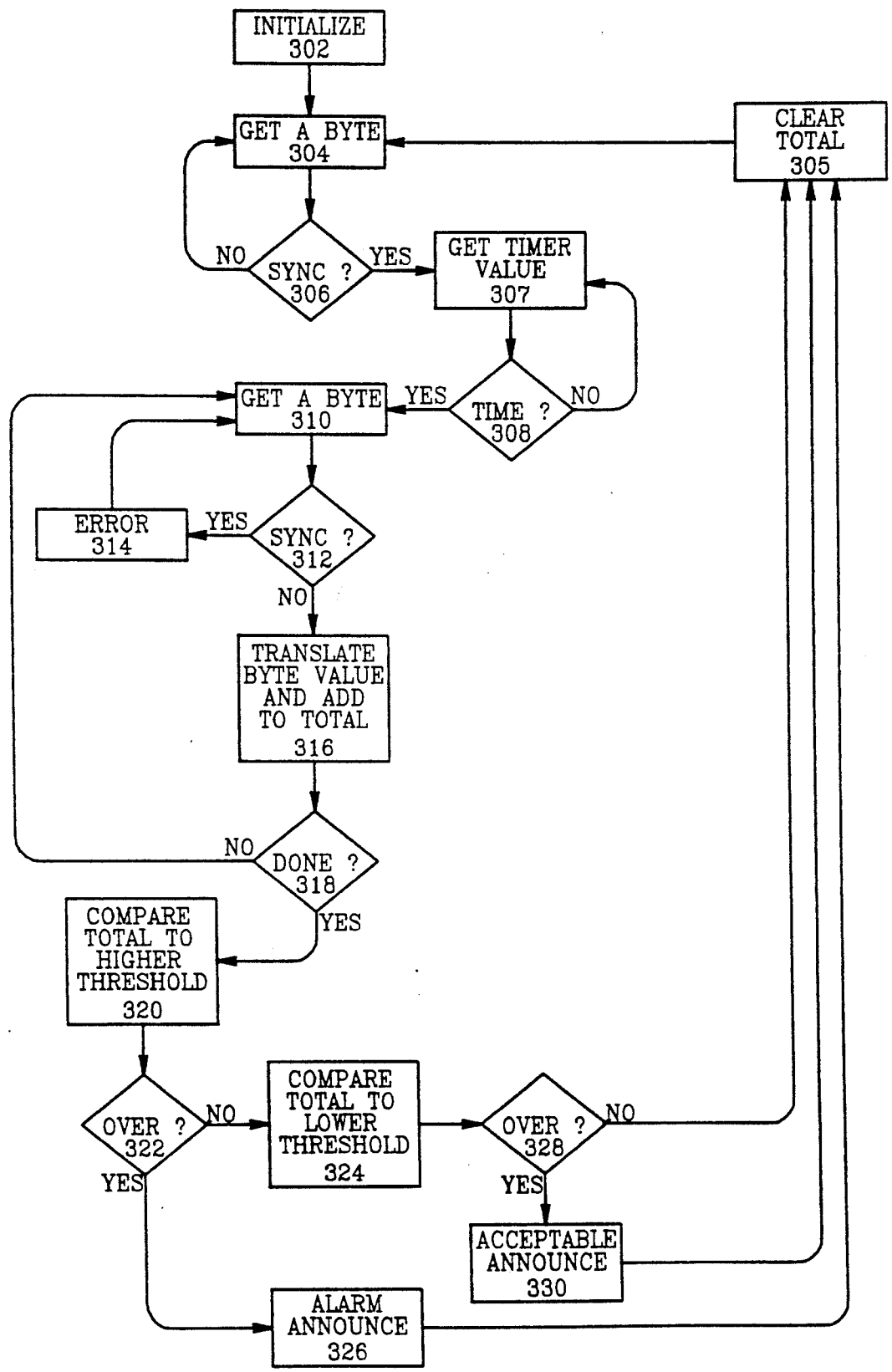
FIG. 12 is a flow chart of a software routine performed by the circuitry of FIG. 11 within the electronic circuit module of FIGS. 1 and 2 to enable the foot force measurement system of the present invention to function as a weight monitor.

Referring now to FIG. 12, there is shown a software program executed by CPU 220 contained within electronic circuit module 500 to facilitate operation of the foot force measurement system of the present invention as a weight monitor. Initialization step 302 is a conventional software initialization step involving setting memory areas to proper values, checking hardware configurations, etc. Step 304 reads one byte of data from the scanning circuitry 210. This data represents either the result of a single instantaneous reading from an individual sensor within force sensor array 100 or a special synchronizing value to mark the beginning or end of a scan of the entire force sensor array 100. Step 306 tests the data byte for the special value. When this value is the special synchronizing value, the next byte of data read will be force data from known sensor of force sensor array 100. The next byte is not read until it is time to do so, as determined by steps 307 and 308. The force sensor array 100 is scanned many times per second. The loop formed by steps 310–318 is executed as many times as there are individual sensors within the force sensor array 100. The current through each of the sensors of force sensor array 100 is measured in a predetermined order and consequently the individual force sensor being addressed can be associated to stored data representing its location within the force sensor array 100. Step 312 tests for the special synchronizing byte, and if it is found at this point in the routine, it is a clear error. Step 314 makes an appropriate data record for future reference, annunciates the error, and resets a loop counter to point to the first sensor.

Step 316 extracts information stored in RAM 250 for the particular sensor of force sensor array 100 currently being evaluated. This information is used to translate the measured current through an individual sensor to a value accurately representing the force being placed on that sensor. This is necessary because the output voltage of each sensor of the force sensor array 100 is inversely and logarithmically proportional to the applied force, and the response varies between individual sensors due to unavoidable manufacturing variances. More specifically, within the RAM 250 is stored a two-vector data array previously loaded by use of a PC and other suitable test equipment. In this array, a first vector applies to each sensor, and a second vector applies to each possible input data value from a particular sensor. Contained in each storage location within the data array is the appropriate output value. Stated in other words, a counter incremented with each iteration of the loop comprising steps 310, 312, 314, 316 and 318 is taken as a first pointer and the value from the sensor measurement is taken as a second pointer to the proper output data stored in the two-vector data array. The value pointed to is added to the value representing the total weight measured by the force sensor array 100. Following execution of the loop comprising step 310, 312, 314, 316, 318 a single scan of the force sensor array 100 has been completed, and the total force on the force sensor array 100 has been computed.

Steps 320, 322, 324, 326, 328, 330 serve to test t e total instantaneous force from the scarf of the force sensor array 100 against two preset values stored in RAM 250. If a "maximum allowable force" (MAF) has been exceeded, a recognizable tone is produced by the annunciator 270. If the total force is less than the MAF, but greater than a predetermined proportion of the MAF, a clearly different tone is produced. If the total force is less than the predetermined proportion of the MAF, no tone is produced. Step 305 clears the storage location for total force. Since the next byte should be a synchronizing byte, it must be wasted. This is done by step 304 before beginning execution of the next loop comprising steps 310, 312, 314, 316, 318.

In use, the foot force measurement system described above is capable of measuring the instantaneous force on all of the individual force sensors within force sensor array 100 during a scan that takes place at regular, predetermined time intervals. The scan rate is fast enough to assure a multiplicity of scans for any foot strike and thus capture any significant instantaneous force value. Consequently, a time-based plot of force on the entire foot or any part thereof may be produced for each foot strike. The force centroid or balance point of forces placed on a foot or portions of a foot may be computed for each scan of force sensor array 100 because the relative position of each of the sensors within force sensor array 100 is fixed. Therefore, a time-based two-coordinate plot of the path of the centroid may be produced for each foot strike. Force placed on the foot in excess of that required to counteract the individual's weight may be assumed to be due to acceleration resulting from work done by that individual. This acceleration can be used to compute an instantaneous resultant velocity from which the mechanical power produced by the individual can be computed. Using these primary measurements and computations, information can be produced which is useful in circumstances including but not limited to those discussed below.

The foot force measurement system of the present invention may be used as a foot force monitor by persons with prosthetic bone or joint implants and fractures who need to carefully control the weight placed on an affected leg during a recovery period. The individual uses crutches or a walker for physical support and, guided by audible tones from the annunciator 270, can control the amount of weight placed on the affected leg. In addition to annunciating individually set optimum and excessive weight thresholds, the foot force measurement system of the present invention also has the capability of generating and storing computer data records which, for example, may include the date and time of system turn on and turn off, and the number of foot strikes of a minimum useful force. When the stored data is reviewed following a period of usage that may extend several weeks, for example, clear indications are provided regarding the extent of system useage and adherence by the wearer to a prescribed course of therapy.

The foot force measurement system of the present invention may also be used to alert the staff of a nursing center when patients who are prone to confusion or are otherwise at risk of falling attempt to stand and walk without assistance. When the patient first places weight on either foot in an effort to stand, the force is detected by the force sensor array 100 fitted into flexible footwear typically worn by such patients. This would trigger a suitable display and annunciation on a computer console located at the central nurses' station to provide an early warning of a patient's attempt to rise from his or her bed.

The foot force measurement system of the present invention may also find application as a guide to fitting and adjustment of a prosthetic leg. It may also be used in training a patient in use of a prosthesis. In this instance, the force sensor array 100 is, of course, placed between the prosthetic foot and a shoe.

The foot force measurement system of the present invention may also be used to provide runners and other athletes instantaneous and continuous measurements of their power output and pace, as measured by frequency of foot strikes. These measurements can be compared to historical values for the current wearer and others so that appropriate and timely adjustments in pace or other running techniques may be made. Deviations of force centroid path or force-time curve from normal values for the individual wearer can be detected. Such deviations imply impending injury, and when they occur, a warning may be sounded in time to avoid an injury.

The foot force measurement system of the present invention may also find application in weight loss programs to monitor the wearer's compliance with an established exercise schedule.

The foot force measurement system of the present invention may be used to detect lower extremity abnormalities or improper footwear and to monitor the result of corrective measures. This is done by comparing a patient's force-time plot(s) and/or the force centroid path plot with normal plots of these parameters. The precise functional information provided by the system of the present invention can be used to quantify and display well-understood anatomical conditions. Use of the present invention to measure and chart a statistically significant number of subjects could produce detailed standards for subsequent comparison not otherwise available. By comparing individual plots with known standards developed through use of the foot force measurement system of the present invention, a wider range of problems could be detected earlier and more accurately than is presently possible.

We claim:

1. A self-contained system for measuring forces applied to the foot of a user, the system comprising:
   a force sensor array positioned within a shoe worn by the user such that said force sensor array lies between the user's foot and an inner sole of the shoe, said force sensor array comprising a multiplicity of individual force sensors arranged in a pattern that covers the entire area of contact between the sole of the user's foot and the inner sole of the shoe;
   an electronic circuit module adapted for attachment to said shoe; and
   interconnection means for electrically coupling the force sensor array to the electronic circuit module;
   said electronic circuit module being operative for electronically continuously scanning said force sensor array to obtain information indicative of an instantaneous force sensed by each one of said multiplicity of individual force sensors comprising said force sensor array;
   said electronic circuit module comprising:
   scanning circuitry for scanning said force sensor array;
   central processing means for executing instructions controlling said scanning circuitry and for processing said information indicative of the instantaneous force sensed by each one of said multiplicity of individual force sensors comprising said force sensor array to obtain force data;
   clock means coupled to said central processing means for providing date and time of day information thereto;
   read-only memory means coupled to said central processing means for storing routines and subroutines of instructions to be executed by said central processing means during a system boot period of operation; and
   random access memory means for storing additional routines and subroutines of instructions to be executed by said central processing means subsequent to said system boot period of operation and for storing said force data.

2. A self-contained system for measuring forces applied to the foot of a user as in claim 1 wherein said electronic circuit module is adapted for removable attachment to a side of said shoe.

3. A self-contained system for measuring forces applied to the foot of a user as in claim 1, further comprising:
   annunciator means for providing an audible signal to the user of certain system operating conditions;
   said central processing means is operative for accumulating said instantaneous force sensed by each one of said multiplicity of individual force sensors and for comparing the accumulated force to a predetermined threshold force and for causing said annunciator means to audibly indicate an accumulated force that exceeds said predetermined threshold force.

4. A self-contained system for measuring forces applied to the foot of a user as in claim 1, further comprising wireless data transmitter means for coupling said central processing means to a remotely located computer to enable the transfer of selected information, including said force data, between said central processing means and said external computer.

5. A self-contained system for measuring forces applied to the foot of a user, the system comprising:
   a force sensor array positioned within a shoe worn by the user such that said force sensor array lies between the user's foot and an inner sole of the shoe, said force sensor array comprising a multiplicity of individual force sensors arranged in a pattern that covers the entire area of contact between the sole of the user's foot and the inner sole of the shoe;
   an electronic circuit module adapted for attachment to said shoe; and
   interconnection means for electrically coupling the force sensor array to the electronic circuit module;
   said electronic circuit module being operative for electronically continuously scanning said force sensor array to obtain information indicative of an instantaneous force sensed by each one of said multiplicity of individual force sensors comprising said force sensor array;

said force sensor array comprising:

top and bottom electrode layers, said top and bottom electrode layers including corresponding pluralities of vertically coincident and horizontally equidistantly spaced individual sensor electrodes, the pluralities of individual sensor electrodes of each of said top and bottom electrode layers being arranged to form substantially parallel equidistant lines of sensor electrodes positioned diagonally with respect to a longitudinal axis of said shoe, the individual sensor electrodes of a given diagonal line of sensor electrodes being electrically serially connected by a conductive trace that follows a nonlinear path;

at least one partially conductive pressure sensitive coating sandwiched between said top and bottom electrode layers;

top and bottom substrate layers overlying said top and bottom electrode layers, respectively, each of said top and bottom substrate layers comprising a lattice structure having a plurality of cutouts in areas not directly overlying said pluralities of individual sensor electrodes; and top and bottom conductive trace layers overlying said top and bottom electrode layers, respectively, each of said top and bottom conductive trace layers including a plurality of conductive traces, each of said conductive traces being electrically connected through a corresponding one of said top and bottom substrate layers to a particular one of the said diagonal lines of sensor electrodes of a corresponding one of said top and bottom electrode layers.

6. A force sensor array adapted for positioning within a shoe to sense the forces applied thereto by the user's foot, the force sensor array comprising:

top and bottom electrode layers, said top and bottom electrode layers including corresponding pluralities of vertically coincident and horizontally equidistantly spaced individual sensor electrodes, the pluralities of individual sensor electrodes of each of said top and bottom electrode layers being arranged to form substantially parallel equidistant lines of sensor electrodes positioned diagonally with respect to a longitudinal axis of said shoe, the individual sensor electrodes of a given diagonal line of sensor electrodes being electrically serially connected by a conductive trace that follows a nonlinear path;

at least one partially conductive pressure sensitive coating sandwiched between said top and bottom electrode layers;

top and bottom substrate layers overlying said top and bottom electrode layers, respectively, each of said top and bottom substrate layers comprising a lattice structure having a plurality of cutouts in areas not directly overlying said pluralities of individual sensor electrodes, each of said top and bottom substrate layers comprising a flexible dielectric film; and top and bottom conductive trace layers overlying said top and bottom electrode layers, respectively, each of said top and bottom conductive trace layers including a plurality of conductive traces, each of said conductive traces being electrically connected through a corresponding one of said top and bottom substrate layers to a particular one of the said diagonal lines of sensor electrodes of a corresponding one of said top and bottom electrode layers.

7. A force sensor array adapted for positioning within a shoe to sense the forces applied thereto by the user's foot, the force sensor array comprising:

top and bottom electrode layers, said top and bottom electrode layers including corresponding pluralities of vertically coincident and horizontally equidistantly spaced individual sensor electrodes, the pluralities of individual sensor electrodes of each of said top and bottom electrode layers being arranged to form substantially parallel equidistant lines of sensor electrodes positioned diagonally with respect to a longitudinal axis of said shoe, the individual sensor electrodes of a given diagonal line of sensor electrodes being electrically serially connected by a conductive trace that follows a nonlinear path;

at least one partially conductive pressure sensitive coating sandwiched between said top and bottom electrode layers;

top and bottom substrate layers overlying said top and bottom electrode layers, respectively, each of said top and bottom substrate layers comprising a lattice structure having a plurality of cutouts in areas not directly overlying said pluralities of individual sensor electrodes, each one of said plurality of cutouts in each of said top and bottom substrate layers being hexagonal in shape; and top and bottom conductive trace layers overlying said top and bottom electrode layers, respectively, each of said top and bottom conductive trace layers including a plurality of conductive traces, each of said conductive traces being electrically connected through a corresponding one of said top and bottom substrate layers to a particular one of the said diagonal lines of sensor electrodes of a corresponding one of said top and bottom electrode layers.

8. A force sensor array adapted for positioning within a shoe to sense the forces applied thereto by the user's foot, the force sensor array comprising:

top and bottom electrode layers, said top and bottom electrode layers including corresponding pluralities of vertically coincident and horizontally equidistantly spaced individual sensor electrodes, the pluralities of individual sensor electrodes of each of said top and bottom electrode layers being arranged to form substantially parallel equidistant lines of sensor electrodes positioned diagonally with respect to a longitudinal axis of said shoe, the individual sensor electrodes of a given diagonal line of sensor electrodes being electrically serially connected by a conductive trace that follows a nonlinear path;

at least one partially conductive pressure sensitive coating sandwiched between said top and bottom electrode layers;

top and bottom substrate layers overlying said top and bottom electrode layers, respectively, each of said top and bottom substrate layers comprising a lattice structure having a plurality of cutouts in areas not directly overlying said pluralities of individual sensor electrodes, each of said top and bottom substrate layers comprising a partially conductive pressure sensitive coating; and top and bottom conductive trace layers overlying said top and bottom electrode layers, respectively, each of said top and bottom conductive trace layers including a plurality of conductive traces, each of said conductive traces being electrically connected through a corresponding one of said top and bottom substrate layers to a particular one of the said diagonal lines of sensor electrodes of a corresponding one of said top and bottom electrode layers.

* * * * *